US006365154B1

(12) United States Patent
Holmes et al.

(10) Patent No.: US 6,365,154 B1
(45) Date of Patent: Apr. 2, 2002

(54) TIE2 AGONIST ANTIBODIES

(75) Inventors: Stephen D. Holmes, Great Chishill (GB); Connie L. Erickson-Miller, Exton; James D. Winkler, Fort Washington, both of PA (US)

(73) Assignees: SmithKline Beecham Corporation, Philadelphia, PA (US); SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/406,532

(22) Filed: Sep. 27, 1999

Related U.S. Application Data

(60) Provisional application No. 60/102,098, filed on Sep. 28, 1998.

(51) Int. Cl.$^7$ .............................................. A61K 39/395

(52) U.S. Cl. .................................. 424/133.1; 424/141.1; 530/300; 530/350; 530/388.1; 530/388.22; 530/389.1; 536/23.1; 536/23.4; 536/23.53

(58) Field of Search ................................. 530/300, 350, 530/388.1, 388.22, 389.1, 391.1; 536/23.1, 23.4, 23.53; 424/133.1, 141.1

(56) References Cited

FOREIGN PATENT DOCUMENTS

WO  WO 95/21866  8/1995  ........... C07K/16/00

OTHER PUBLICATIONS

MPSRCH result 1 for SEQ ID:5, Hagiwara Y. JP–272950 (1995).*
MPSRCH result 3 for SEQ ID: 15; Mochly–Rosen et al. WO 95/21252 (1995).*
MPSRCH result 1 for SEQ ID:19; Bosslet et al. DE–4133791 (1993).*
Bauters et al., "Recovery of Disturbed Endothelium–Dependent Flow in the Collateral–Perfused Rabbitt . . . Vascular EndothelialGrowth Factor", *Circulation*, vol. 91, pp. 2802–2809 (1995).
Bauters et al., "Site–specific Therapeutic Angiogeneis After Systemic Administration of Vascular Endothelial Growth Factor", *Journal of Vascular Surgery*, vol. 21, pp. 314–324 (1995).
Isner et al., "Arterial Gene Transfer for Therapeutic Angiogenesis in Patients with Peripheral Artery Disease", *Human Gene Therapy*, vol. 7, pp. 959–988 (1996).
Takeshita et al., "Therapeutic Angiogenesis Following Arterial Gene . . . Factor in a Rabbit . . . Ischemia", *Biochemical and Biophysical Research Communications*, vol. 227, pp. 628–635 (1996).
Tsurumi et al., "Treatment of Acute Limb Ischemia by Intramuscular Injection of Vascular Endothelial Growth Factor Gene", *Circulation*, vol. 96, pp. 382–388 (1997).

Korhonen et al., "Enhanced Expression of the *tie* Receptor Tyrosine Kinase in Endothelial Cells During Neovascularization", *Blood*, vol. 80, No. 10, pp. 2548–2555 (1992).
Schlaeger et al., "Vascular Endothelial Cell Lineage–Specific Promoter in Transgenic Mice", *Development*, vol. 121, pp. 1089–1098 (1995).
Kapoainen et al., "Enhanced Expression of the Tie Receptor Tyrosine Kinase Messenger RNA in the Vascular Endothelium of Metastatic Melanomas", *Cancer Research*, vol. 54, pp. 6571–6577 (1994).
Dumont et al., "Dominant–negative and Targeted Null Mutations in the Endothelial Receptor . . . Vasculogenesis of the Embryo", *Genes & Development*, vol. 8, pp. 1897–1909 (1994).
Sato et al., "Distant Roles of the Receptor Tyrosine Kinases Tie–1 and Tie–2 in Blood Vessel Formation", *Nature*, vol. 376, pp. 70–74 (1995).
Davis et al., "Isolation of Angiopoietin–1, a Ligand for the TIE2 Receptor, by Secretion–Trap Expression Cloning", *Cell*, vol. 87, pp. 1161–1169 (1996).
Suri et al., "Requisite Role of Angiopoietin–1, a Ligand for the TIE2 Receptor, during Embryonic Angiogensis", *Cell*, vol. 87, pp. 1171–1180 (1996).
Maisonpierre et al., "Angiopoietin–2, a Natural Antagonist for Tie2 That Disrupts in vivo Angiogenesis", *Science*, vol. 277, pp. 55–60 (1997).
Dumont et al., "The Endothelial–specific Receptor Tyrosine Kinase, tek, is a Member of a New Subfamily of Receptors", *Oncogene*, vol. 8, pp. 1293–1301 (1993).
Partanen et al., "A Novel Endothelial Cell Surface Receptor Tyrosine Kinase . . . Epidermal Growth Factor Homology Domains", *Molecular and Cellular Biology*, pp. 1698–1707 (1992).
Sato et al., "tie–1 and tie–2 Define Another Class of Putative Receptor Tyrosine Kinase Genes . . . Early Embryonic Vascular System", *Proc. Natl. Acad. Sci. USA*, vol. 90, pp. 9355–9358 (1993).
Kukk et al., "Analysis of Tie Receptor Tyrosine Kinase in Haemopoietic Progenitor and Leukaemia Cells", *British Journal of Haematology*, vol. 98, pp. 195–203 (1997).
Batard et al., "The Tie Receptor Tyrosine Kinase is Expressed by Human Hematopoietic Progenitor Cells and by a Subset of Megakaryocytic Cells", *Blood*, vol. 87, pp. 2212–2220 (1996).

(List continued on next page.)

*Primary Examiner*—James Housel
*Assistant Examiner*—Ulrike Winkler
(74) *Attorney, Agent, or Firm*—Kirk Baumeister; William T. King

(57) ABSTRACT

Tie2 receptor agonist antibodies, their use in enhancing angiogenesis and other uses are disclosed.

27 Claims, 1 Drawing Sheet

OTHER PUBLICATIONS

Chabot et al., "The Proto–oncogene c–kit Encoding a Transmembrane Tyrosine Kinase Receptor maps to the Mouse W Locus", *Nature*, vol. 335, pp. 88–89 (1988).

Yarden et al., "Human Proto–oncogene c–kit: A New Cell Surface Receptor Tyrosine Kinase for an Unidentified Ligand", *The EMBO Journal*, vol. 6, No. 11, pp. 3341–3351 (1987).

Matthews et al., "A Receptor Tyrosine Kinase Specific to Hematopoietic Stem and Progenitor Cell–Enriched Populations", *Cell*, vol. 65, pp. 1143–1152 (1991).

Tillman et al., "Both IgM and IgG Anti–DNA Antibodies Are The Products of Clonally Selective B Cell Stimulation in (NZB x NZW)$F_1$ Mice", *J. Exp. Med.*, vol. 176, pp. 761–779 (1992).

Monestier et al., "Molecular Analysis of Mercury–Induced Antinucleolar Antibodies in $H-2^S$ Mice", *Journal of Immunology*, vol. 152, pp. 667–675 (1994).

* cited by examiner

SEQUENCE LISTING

```
<160> NUMBER OF SEQ ID NOS:  21

<210> SEQ ID NO 1
<211> LENGTH: 357
<212> TYPE: DNA
<213> ORGANISM: Mus musculus
<220> FEATURE:
<221> NAME/KEY: CDS
<222> LOCATION: (1)...(357)
<223> OTHER INFORMATION: 15B8 heavy chain v region

<400> SEQUENCE: 1 caa gtt cag ctg cag cag cct ggg gtt gta ctt gtg atg cct ggg gct        48
Gln Val Gln Leu Gln Gln Pro Gly Val Val Leu Val Met Pro Gly Ala
 1               5                  10                  15 tca gtg aag ctg tcc tgc aag gct tct ggc tac acc ttc gcc agc tac        96
Ser Val Lys Leu Ser Cys Lys Ala Ser Gly Tyr Thr Phe Ala Ser Tyr
            20                  25                  30 tgg atg cac tgg gtg aag cag agg cct gga caa ggc ctt gag tgg atc       144
Trp Met His Trp Val Lys Gln Arg Pro Gly Gln Gly Leu Glu Trp Ile
        35                  40                  45 gga gag att gat cct tct gat agt tat cgt aac tac aat caa aag ttc       192
Gly Glu Ile Asp Pro Ser Asp Ser Tyr Arg Asn Tyr Asn Gln Lys Phe
    50                  55                  60 aag ggc aag gcc aca ttg act gta gac aaa tcc tcc agc aca gtc aat       240
Lys Gly Lys Ala Thr Leu Thr Val Asp Lys Ser Ser Ser Thr Val Asn
65                  70                  75                  80 atg cag ctc agc agc ctg aca tct gag gac tct gcg gtc tat tac tgt       288
Met Gln Leu Ser Ser Leu Thr Ser Glu Asp Ser Ala Val Tyr Tyr Cys
                85                  90                  95 gca aag acg tcg gga ata ggg agg gct atg gac tac tgg ggt caa gga       336
Ala Lys Thr Ser Gly Ile Gly Arg Ala Met Asp Tyr Trp Gly Gln Gly
            100                 105                 110
```

```
acc tca gtc acc gtc tcc tca                                              357
Thr Ser Val Thr Val Ser Ser
        115
```

<210> SEQ ID NO 2
<211> LENGTH: 119
<212> TYPE: PRT
<213> ORGANISM: Mus musculus

<400> SEQUENCE: 2

```
Gln Val Gln Leu Gln Gln Pro Gly Val Val Leu Val Met Pro Gly Ala
 1               5                  10                  15

Ser Val Lys Leu Ser Cys Lys Ala Ser Gly Tyr Thr Phe Ala Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Arg Asn Tyr Asn Gln Lys Phe
    50                  55                  60

Lys Gly Lys Ala Thr Leu Thr Val Asp Lys Ser Ser Thr Val Asn
65                  70                  75                  80

Met Gln Leu Ser Ser Leu Thr Ser Glu Asp Ser Ala Val Tyr Tyr Cys
                85                  90                  95

Ala Lys Thr Ser Gly Ile Gly Arg Ala Met Asp Tyr Trp Gly Gln Gly
            100                 105                 110

Thr Ser Val Thr Val Ser Ser
        115
```

<210> SEQ ID NO 3
<211> LENGTH: 321
<212> TYPE: DNA
<213> ORGANISM: Mus musculus
<220> FEATURE:
<221> NAME/KEY: CDS
<222> LOCATION: (1)...(321)
<223> OTHER INFORMATION: 15B8 light chain v region

<400> SEQUENCE: 3

```
gat att cag atg att cag tct cca gcc tcc cta tct gca tct gtg gga        48
Asp Ile Gln Met Ile Gln Ser Pro Ala Ser Leu Ser Ala Ser Val Gly
 1               5                  10                  15 gaa act gtc acc atc aca tgt cga gca agt gaa aat att tac agt ttt       96
Glu Thr Val Thr Ile Thr Cys Arg Ala Ser Glu Asn Ile Tyr Ser Phe
            20                  25                  30 gta aca tgg tat cag cag aaa cag gga aag tct cct cag ctc ctg gtc      144
Val Thr Trp Tyr Gln Gln Lys Gln Gly Lys Ser Pro Gln Leu Leu Val
        35                  40                  45 ttt aat gca aaa aac tta gta gag ggt gtg cca tca agc ttc agt ggc      192
Phe Asn Ala Lys Asn Leu Val Glu Gly Val Pro Ser Ser Phe Ser Gly
    50                  55                  60 agt gga tca ggc aca cag ttc tct ctg aag atc gac agc cta cag cct      240
Ser Gly Ser Gly Thr Gln Phe Ser Leu Lys Ile Asp Ser Leu Gln Pro
65                  70                  75                  80 gaa gat ttt ggg act tat tac tgt caa cat cat tat agt atc ccg tac      288
Glu Asp Phe Gly Thr Tyr Tyr Cys Gln His His Tyr Ser Ile Pro Tyr
                85                  90                  95 acg ttc gga ggg ggg acc aag ctg gag atg aga                          321
Thr Phe Gly Gly Gly Thr Lys Leu Glu Met Arg
            100                 105
```

<210> SEQ ID NO 4
<211> LENGTH: 107

```
<212> TYPE: PRT
<213> ORGANISM: Mus musculus

<400> SEQUENCE: 4

Asp Ile Gln Met Ile Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Phe
                20                  25                  30

Val Thr Trp Tyr Gln Gln Lys Gln Gly Lys Ser Pro Gln Leu Leu Val
            35                  40                  45

Phe Asn Ala Lys Asn Leu Val Glu Gly Val Pro Ser Ser Phe Ser Gly
     50                  55                  60

Ser Gly Ser Gly Thr Gln Phe Ser Leu Lys Ile Asp Ser Leu Gln Pro
65                  70                  75                  80

Glu Asp Phe Gly Thr Tyr Tyr Cys Gln His His Tyr Ser Ile Pro Tyr
                85                  90                  95

Thr Phe Gly Gly Gly Thr Lys Leu Glu Met Arg
                100                 105

<210> SEQ ID NO 5
<211> LENGTH: 5
<212> TYPE: PRT
<213> ORGANISM: Mus musculus
<220> FEATURE:
<221> NAME/KEY: SITE
<222> LOCATION: (1)...(5)
<223> OTHER INFORMATION: 15B8 heavy chain CDR 1

<400> SEQUENCE: 5

Ser Tyr Trp Met His
 1               5

<210> SEQ ID NO 6
<211> LENGTH: 17
<212> TYPE: PRT
<213> ORGANISM: Mus musculus
<220> FEATURE:
<221> NAME/KEY: SITE
<222> LOCATION: (1)...(17)
<223> OTHER INFORMATION: 15B8 heavy chain CDR 2

<400> SEQUENCE: 6

Glu Ile Asp Pro Ser Asp Ser Tyr Arg Asn Tyr Asn Gln Lys Phe Lys
 1               5                  10                  15
Gly

<210> SEQ ID NO 7
<211> LENGTH: 10
<212> TYPE: PRT
<213> ORGANISM: Mus musculus
<220> FEATURE:
<221> NAME/KEY: SITE
<222> LOCATION: (1)...(10)
<223> OTHER INFORMATION: 15B8 heavy chain CDR 3

<400> SEQUENCE: 7

Thr Ser Gly Ile Gly Arg Ala Met Asp Tyr
 1               5                  10

<210> SEQ ID NO 8
<211> LENGTH: 11
<212> TYPE: PRT
<213> ORGANISM: Mus musculus
<220> FEATURE:
```

```
<221> NAME/KEY: SITE
<222> LOCATION: (1)...(11)
<223> OTHER INFORMATION: 15B8 light chain CDR 1

<400> SEQUENCE: 8

Arg Ala Ser Glu Asn Ile Tyr Ser Phe Val Thr
 1               5                  10

<210> SEQ ID NO 9
<211> LENGTH: 7
<212> TYPE: PRT
<213> ORGANISM: Mus musculus
<220> FEATURE:
<221> NAME/KEY: SITE
<222> LOCATION: (1)...(7)
<223> OTHER INFORMATION: 15B8 light chain CDR 2

<400> SEQUENCE: 9

Asn Ala Lys Asn Leu Val Glu
 1               5

<210> SEQ ID NO 10
<211> LENGTH: 9
<212> TYPE: PRT
<213> ORGANISM: Mus musculus
<220> FEATURE:
<221> NAME/KEY: SITE
<222> LOCATION: (1)...(9)
<223> OTHER INFORMATION: 15B8 light chain CDR 3

<400> SEQUENCE: 10

Gln His His Tyr Ser Ile Pro Tyr Thr
 1               5

<210> SEQ ID NO 11
<211> LENGTH: 336
<212> TYPE: DNA
<213> ORGANISM: Mus musculus
<220> FEATURE:
<221> NAME/KEY: CDS
<222> LOCATION: (1)...(336)
<223> OTHER INFORMATION: 13H10 heavy chain v region beginning at
      amino acid 7

<400> SEQUENCE: 11 tct gga cct gaa ctg aag aag cct gga gag aca gtc aag atc tcc tgc      48
Ser Gly Pro Glu Leu Lys Lys Pro Gly Glu Thr Val Lys Ile Ser Cys
 1               5                  10                  15 aag gct tct ggt tat acc ttc aca gac ttt tca ata cac tgg gtg aag      96
Lys Ala Ser Gly Tyr Thr Phe Thr Asp Phe Ser Ile His Trp Val Lys
                20                  25                  30 cag gct cca gga aag ggt tta aag tgg atg ggc tgg ata aac act gag     144
Gln Ala Pro Gly Lys Gly Leu Lys Trp Met Gly Trp Ile Asn Thr Glu
            35                  40                  45 act ggt gag aca aca tat gca gaa gac ttc aag gga cgg ttt gcc ttc     192
Thr Gly Glu Thr Thr Tyr Ala Glu Asp Phe Lys Gly Arg Phe Ala Phe
        50                  55                  60 tct ttg gaa acc tct gcc agc act gcc tac ttg caa atc aac aac ctc     240
Ser Leu Glu Thr Ser Ala Ser Thr Ala Tyr Leu Gln Ile Asn Asn Leu
65                  70                  75                  80 aaa aat gag gac acg gct aca tat ttt tgt agt aga agg tat gat tac     288
Lys Asn Glu Asp Thr Ala Thr Tyr Phe Cys Ser Arg Arg Tyr Asp Tyr
                85                  90                  95 gac acc tgg ttt gct tac tgg ggc caa ggg act ctg gtc act gtc tct     336
Asp Thr Trp Phe Ala Tyr Trp Gly Gln Gly Thr Leu Val Thr Val Ser
            100                 105                 110
```

```
<210> SEQ ID NO 12
<211> LENGTH: 112
<212> TYPE: PRT
<213> ORGANISM: Mus musculus

<400> SEQUENCE: 12

Ser Gly Pro Glu Leu Lys Lys Pro Gly Glu Thr Val Lys Ile Ser Cys
 1               5                  10                  15

Lys Ala Ser Gly Tyr Thr Phe Thr Asp Phe Ser Ile His Trp Val Lys
             20                  25                  30

Gln Ala Pro Gly Lys Gly Leu Lys Trp Met Gly Trp Ile Asn Thr Glu
         35                  40                  45

Thr Gly Glu Thr Thr Tyr Ala Glu Asp Phe Lys Gly Arg Phe Ala Phe
 50                  55                  60

Ser Leu Glu Thr Ser Ala Ser Thr Ala Tyr Leu Gln Ile Asn Asn Leu
 65                  70                  75                  80

Lys Asn Glu Asp Thr Ala Thr Tyr Phe Cys Ser Arg Arg Tyr Asp Tyr
                 85                  90                  95

Asp Thr Trp Phe Ala Tyr Trp Gly Gln Gly Thr Leu Val Thr Val Ser
            100                 105                 110

<210> SEQ ID NO 13
<211> LENGTH: 339
<212> TYPE: DNA
<213> ORGANISM: Mus musculus
<220> FEATURE:
<221> NAME/KEY: CDS
<222> LOCATION: (1)...(339)
<223> OTHER INFORMATION: 13H10 light chain v region

<400> SEQUENCE: 13 gat atc gtg atg act cag gct gca ctc tct gta cct gtc act cct gga      48
Asp Ile Val Met Thr Gln Ala Ala Leu Ser Val Pro Val Thr Pro Gly
 1               5                  10                  15 gag tca gta tcc atc tcc tgc agg tcg agt agt agt ctc ctg cat aga      96
Glu Ser Val Ser Ile Ser Cys Arg Ser Ser Ser Ser Leu Leu His Arg
             20                  25                  30 aat ggc aac act tac ttg tat tgg ttc ctg cag agg cca ggg cag tct     144
Asn Gly Asn Thr Tyr Leu Tyr Trp Phe Leu Gln Arg Pro Gly Gln Ser
         35                  40                  45 cct cag ctc ctg ata tat cgg atg tcc aac ctt gcc tca gga gtc cca     192
Pro Gln Leu Leu Ile Tyr Arg Met Ser Asn Leu Ala Ser Gly Val Pro
     50                  55                  60 gac agg ttc agt ggc agt ggg tca gga act gct ttc aca ctg aga atc     240
Asp Arg Phe Ser Gly Ser Gly Ser Gly Thr Ala Phe Thr Leu Arg Ile
 65                  70                  75                  80 agt aga gtg gag gct gag gat gtg ggt gtt tat tac tgt atg caa cgt     288
Ser Arg Val Glu Ala Glu Asp Val Gly Val Tyr Tyr Cys Met Gln Arg
                 85                  90                  95 cta gaa tat cct ttc acg ttc gga ggg ggg acc aag ctg gaa ata aaa     336
Leu Glu Tyr Pro Phe Thr Phe Gly Gly Gly Thr Lys Leu Glu Ile Lys
            100                 105                 110 cgg                                                                  339
Arg

<210> SEQ ID NO 14
<211> LENGTH: 113
<212> TYPE: PRT
<213> ORGANISM: Mus musculus
```

```
<400> SEQUENCE: 14

Asp Ile Val Met Thr Gln Ala Ala Leu Ser Val Pro Val Thr Pro Gly
 1               5                  10                  15

Glu Ser Val Ser Ile Ser Cys Arg Ser Ser Ser Leu Leu His Arg
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln Arg
                85                  90                  95

Leu Glu Tyr Pro Phe Thr Phe Gly Gly Gly Thr Lys Leu Glu Ile Lys Arg
            100                 105                 110

<210> SEQ ID NO 15
<211> LENGTH: 5
<212> TYPE: PRT
<213> ORGANISM: Mus musculus
<220> FEATURE:
<221> NAME/KEY: SITE
<222> LOCATION: (1)...(5)
<223> OTHER INFORMATION: heavy chain CDR 1

<400> SEQUENCE: 15

Asp Phe Ser Ile His
 1               5

<210> SEQ ID NO 16
<211> LENGTH: 17
<212> TYPE: PRT
<213> ORGANISM: Mus musculus
<220> FEATURE:
<221> NAME/KEY: SITE
<222> LOCATION: (1)...(17)
<223> OTHER INFORMATION: heavy chain CDR 2

<400> SEQUENCE: 16

Trp Ile Asn Thr Glu Thr Gly Glu Thr Thr Tyr Ala Glu Asp Phe Lys
 1               5                  10                  15

Gly

<210> SEQ ID NO 17
<211> LENGTH: 10
<212> TYPE: PRT
<213> ORGANISM: Mus musculus
<220> FEATURE:
<221> NAME/KEY: SITE
<222> LOCATION: (1)...(10)
<223> OTHER INFORMATION: heavy chain CDR 3

<400> SEQUENCE: 17

Arg Tyr Asp Tyr Asp Thr Trp Phe Ala Tyr
 1               5                  10

<210> SEQ ID NO 18
<211> LENGTH: 16
<212> TYPE: PRT
<213> ORGANISM: Mus musculus
<220> FEATURE:
<221> NAME/KEY: SITE
<222> LOCATION: (1)...(16)
<223> OTHER INFORMATION: light chain CDR 1
```

```
<400> SEQUENCE: 18

Arg Ser Ser Ser Leu Leu His Arg Asn Gly Asn Thr Tyr Leu Tyr
 1               5                  10                  15

<210> SEQ ID NO 19
<211> LENGTH: 7
<212> TYPE: PRT
<213> ORGANISM: Mus musculus
<220> FEATURE:
<221> NAME/KEY: SITE
<222> LOCATION: (1)...(7)
<223> OTHER INFORMATION: light chain CDR 2

<400> SEQUENCE: 19

Arg Met Ser Asn Leu Ala Ser
 1               5

<210> SEQ ID NO 20
<211> LENGTH: 9
<212> TYPE: PRT
<213> ORGANISM: Mus musculus
<220> FEATURE:
<221> NAME/KEY: SITE
<222> LOCATION: (1)...(9)
<223> OTHER INFORMATION: light chain CDR 3

<400> SEQUENCE: 20

Met Gln Arg Leu Glu Tyr Pro Phe Thr
 1               5

<210> SEQ ID NO 21
<211> LENGTH: 118
<212> TYPE: PRT
<213> ORGANISM: Mus musculus
<220> FEATURE:
<221> NAME/KEY: PEPTIDE
<222> LOCATION: (1)...(118)
<223> OTHER INFORMATION: Complete 13H10 heavy chain v region

<400> SEQUENCE: 21

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asp Phe
            20                  25                  30

Ser Ile His Trp Val Lys Gln Ala Pro Gly Lys Gly Leu Lys Trp Met
        35                  40                  45

Gly Trp Ile Asn Thr Glu Thr Gly Glu Thr Thr Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Arg Arg Tyr Asp Tyr Asp Thr Trp Phe Ala Tyr Trp Gly Gln Gly
            100                 105                 110

Thr Leu Val Thr Val Ser
        115
```

TIE2 AGONIST ANTIBODIES

This application claims the benefit of U.S. Provisional Application No. 60/102,098, filed Sep. 28, 1998.

FIELD OF THE INVENTION

This invention relates to agonist monoclonal antibodies (mAb) that bind to the Tie2 receptor and to the use of such antibodies for therapeutic purposes.

BACKGROUND OF THE INVENTION

Angiogenesis or neovascularisation is the process of development of new or replacement blood vessels. It is a necessary and normal process by which the vasculature is established in the embryo. Angiogenesis does not occur, in general, in most normal adult tissues, exceptions being sites of ovulation, menses and wound healing.

Increasing blood supply is beneficial in many conditions such as ischemic conditions, resulting from stroke, myocardial infarction and other infarctions, and states of poor blood flow, resulting from diseases such as diabetes or peripheral vascular diseases. Vascular endothelial growth factor and basic fibroblast growth factor are factors that have been shown to promote angiogenesis. Recent work with vascular endothelial growth factor (VEGF) and basic fibroblast growth factor has demonstrated that promotion of angiogenesis by these factors can have benefit in ischemic diseases and vascular disease (Bauters, C. et al., Circulation, 91: 2802–2809, 1995; Bauters, C. et al., Journal of Vascular Surgery, 21: 314–24, 1995; Isner, J. M. et al., Human Gene Therapy, 7: 959–988, 1996; Takeshita, S., et al., Biochemical &. Biophysical Research Communications, 227: 628–635, 1996; Tsurumi, Y., et al., Circulation, 96: 382–388, 1997).

In recent years, it has become clear that while angiogenesis is a complex, multicellular phenomena, specific ligands and their receptors play a key role. In particular, a combination of studies suggest that the Tie2 receptor and its ligand are important in angiogenesis.

Tie2 receptor has been located in endothelial cells of all forming blood vessels and in the endocardium of mouse embryos (Korhonen et al., Blood 80:2548–2555, 1992). Selective patterns of expression in endothelial cells during embryonic development has also been demonstrated (Schlaeger et al., Development 121:1089–1098, 1995).

In adult tissues, Tie mRNA cannot be observed in skin, except at sites of active wound healing where the proliferating capillaries in the granulation tissue contain abundant Tie mRNA (Korhonen et al., Blood 80:2548–2555, 1992). Further, Tie receptor is expressed in the vascular endothelium of metastasizing melanomas (Kaipainen et al., Cancer Res. 54:6571–6577, 1994). While Tie receptor expression is down-regulated in the established vasculature, it is upregulated in angiogenesis that occurs in the ovary during ovulation, in wounds and in tumor (breast, melanoma and renal cell carcinoma) vasculature, consistent with prevailing views that angiogenesis in the adult borrows from embryonic angiogenic mechanisms.

Homozygous mice with a Tie2 knockout, or carrying a transgene encoding a "dominant-negative" Tie2 receptor, confirmed that the Tie2 receptor is critical for embryonic development (Dumont et al., Genes Dev. 8:1897–1909, 1994; Sato et al., Nature 376:70 . 74, 1995). Embryonic death in these mice occurred due to vascular insufficiency and there were dramatically reduced numbers of endothelial cells. Vasculogenesis—that is the differentiation of endothelial cells and the in situ formation of vessels—appeared relatively normal in mice lacking Tie2. The subsequent sprouting and remodeling resulting in formation of vessel branches (angiogenesis) was drastically reduced in the Tie2 mutant mice embryos. This lack of sprouting and angiogenesis resulted in substantial growth retardation, particularly of the brain, neural tube and heart, resulting in lack of viability. These results exemplify the critical importance of Tie2 in angiogenesis. This is significant, as angiogenesis is regulated by a number of growth factors. Interestingly, Flk1 (VEGF receptor) knockout mice exhibit embryo lethal defects in vasculogenesis, that occur earlier than those of Tie2 disruption. Disruption of the Tie1 receptor yields a much different, and later, defective phenotype; the mouse embryo dies late in development due to hemorrhage resulting from defective integrity of an otherwise well-formed vasculature. Taken together, these studies suggest that the VEGF/Flk1 and Tie systems operate in sequential fashion, with Tie2 having a critical role in angiogenesis.

Recently, two ligands for the Tie2 receptor have been reported. Angiopoietin-1 binds and induces the tyrosine phosphorylation of Tie2 and its expression in vivo is in close proximity with developing blood vessels (Davis et al., Cell 87:1161–1169,1996). Mice engineered to lack Angiopoietin-1 display angiogenic deficits reminiscent of those previously seen in mice lacking Tie2 receptors, demonstrating that Angiopoietin-1 is a primary physiologic ligand for Tie2 and that Tie2 has critical in vivo angiogenic actions (Suri et al., Cell 87:1171–1180, 1996). Angiopoietin-2 was identified by homology screening and shown to be a naturally occurring antagonist for Tie2 receptors. Transgenic overexpression of Angiopoietin-2 disrupts blood vessel formation in the mouse embryo (Maisonpierre et al., Science 277:55–60, 1997). Together, these results support a role for Tie2 receptors in angiogenesis.

The Tie1 and Tie2 receptors are single-transmembrane, tyrosine kinase receptors (Tie stands for Tyosine kinase receptors with immunoglobulin and EGF homology domains). They are the only receptor tyrosine kinases, other than those receptors for VEGF, that are largely restricted to endothelial cells in their expression. Both have been cloned and reported by several groups (Dumont et al., Oncogene 8:1293–1301, 1993; Partanen et al., Mol. Cell Biol. 12:1698–1707, 1992; Sato et al., Proc. Natl. Acad. Sci. USA 90:9355–9358, 1993).

The Tie receptors are proteins of approximately 125 kDa, with a single putative transmembrane region. The extracellular domain of these receptors is uniquely divided into three regions that have a pattern of cysteine expression found in EGF-like domains; two regions that have some weak homology to and structural characteristics of immunoglobulin-like domains; and three regions with homology to the fibronectin III repeat structure. The intracellular portion of Tie2 is most closely related (~40% identity) to the kinase domains of FGF-R1, PDGF-R and c-kit. The intracellular portions of Tie2 contain all of the features of tyrosine kinases, including a GXGXXG ATP binding site consensus sequence and typical tyrosine kinase motifs (i.e., HRDLAARN and DFGL).

Based upon the importance of Tie2 receptors in angiogenesis, Tie2 receptor agonist activity is predicted to stimulate angiogenesis, providing disease-specific therapeutic effects. Clearly, there is a need to develop high affinity, potent agonist antibodies to the Tie2 receptor which will have sufficient activity to work in vivo at therapeutically acceptable concentrations.

Tie2 receptors are expressed on hematopoietic progenitors, including CD34+ cells, megakaryocyte progenitors and megakaryocyte-derived cell lines (Kukk et al., Brit J Haematol. 98:195–203, 1997; Batard et al., Blood 87:2212–2220, 1996). The Tie2 receptor has homology to other hematopoietic growth factor receptors such as c-kit (Chabot et al, Nature 335:88, 1988; Yarden et al., EMBO J 6:3341, 1987) and flk-2 (Matthews et al, Cell 65:1143, 1991). The expression of Tie2 decreased on more mature hematopoietic cells, although it was maintained on a significant fraction of cells during megakaryocytic differentiation (Batard). These data, taken together, suggest that Tie2 is a receptor for a hematopoietic growth factor acting on early progenitors and during differentiation of the megakaryocytic lineage.

SUMMARY OF THE INVENTION

One aspect of the present invention is a Tie2 receptor agonist antibody having the identifying characteristics of monoclonal antibody 15B8 or 13H10.

Another aspect of the invention is an antibody comprising a heavy chain variable region polypeptide as set forth in SEQ ID NO: 2 and a light chain variable region polypeptide as set forth in SEQ ID NO: 4 and isolated polynucleotides encoding them.

Another aspect of the invention is a heavy chain CDR having an amino acid sequence as set forth in SEQ ID NO: 5, 6 or 7.

Another aspect of the invention is a light chain CDR having an amino acid sequence as set forth in SEQ ID NO: 8, 9 or 10.

Another aspect of the invention is an antibody comprising a heavy chain variable region polypeptide as set forth in SEQ ID NO: 21 and a light chain variable region polypeptide as set forth in SEQ ID NO: 14 and isolated polynucleotides encoding them.

Another aspect of the invention is a heavy chain CDR having an amino acid sequence as set forth in SEQ ID NO: 15, 16 or 17.

Another aspect of the invention is a light chain CDR having an amino acid sequence as set forth in SEQ ID NO: 18, 19 or 20.

Another aspect of the invention is a hybridoma having the identifying characteristics of cell line 15B8 or 13H10.

Another aspect of the invention is a method for enhancing angiogenesis in a animal comprising administering an effective dose of an Tie2 receptor agonist antibody having the identifying characteristics of monoclonal antibody 15B8 or 13H10.

Another aspect of the invention is a method for enhancing endothelial cell survival in a mammal comprising administering an effective dose of a Tie2 receptor agonist antibody.

Another aspect of the invention is a method of enhancing hematopoietic or megakaryocytic cell proliferation in a mammal comprising administering an effective dose of a Tie2 receptor agonist antibody.

DETAILED DESCRIPTION OF THE INVENTION

Figure 1:
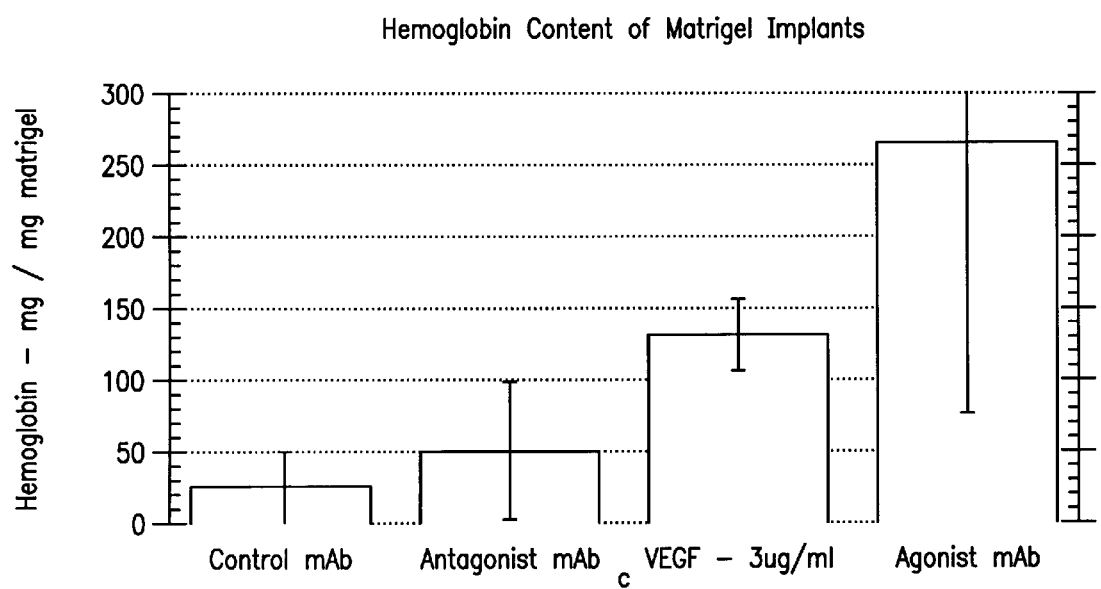
FIG. 1 is a graph of experimental results demonstrating the activity of monoclonal antibody 15B8 in the Matrigel vascularization model.

All publications, including but not limited to patents and patent applications, cited in this specification are herein incorporated by reference as though fully set forth.

As used herein, the term "enhancing angiogenesis" means increasing the development of new or replacement blood vessels (neovascularization).

As used herein, the term "agonist activity" refers to the activity of an antibody that binds to Tie2 receptor and enhances angiogenesis.

As used herein, the term "treating" and derivatives thereof means prophylactic, palliative or therapeutic therapy.

The present invention provides a variety of antibodies, including altered antibodies and fragments thereof directed against Tie2 receptor, which are characterized by agonist activity. Exemplary Tie2 receptor agonist antibodies are the murine monoclonal antibodies 15B8 or 13H10.

"Antibodies" refers to immunoglobulins which can be prepared by conventional hybridoma techniques, phage display combinatorial libraries, immunoglobulin chain shuffling and humanization techniques. Also included are fully human monoclonal antibodies. As used herein, "antibody" also includes "altered antibody" which refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, Fab' or F(ab')$_2$ and the like. These antibody products are useful in therapeutic and pharmaceutical compositions for treating acute and chronic ischemic and vascular insufficiency diseases and other conditions where increased blood flow is indicated. Exemplary ischemic diseases include myocardial infarction and cerebral stroke. Exemplary vascular insufficiency diseases include diabetes.

"Altered immunoglobulin coding region" refers to a nucleic acid sequence encoding an altered antibody of the invention. When the altered antibody is a complementarity determining region-grafted (CDR-grafted) or humanized antibody, the sequences that encode the CDRs from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. in "Sequences of Proteins of Immunological Interest", 4th Ed., U.S. Department of Health and Human Services, National Institutes of Health (1987) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably, it is an immunoglobulin gene. The second immunoglobulin partner may include a nucleic acid sequence encoding the entire constant region for the same (i.e., homologous, where the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, Fab' or F(ab')$_2$ are used with their standard meanings. See, e.g., Harlow et al. in "Antibodies A Laboratory Manual", Cold Spring Harbor Laboratory, (1988).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulins. In addition, framework support residues may be altered to preserve binding affinity. See, e.g., Queen et al., *Proc. Natl Acad Sci USA*, 86, 10029–10032 (1989), Hodgson et al., *Bio/Technology* 9, 421 (1991). Furthermore, as decribed herein, additional residues may be altered to preserve the agonist activity of the donor antibody.

The term "donor antibody" refers to a monoclonal or recombinant antibody which contributes the nucleic acid sequences of its variable regions, CDRs or other functional fragments or analogs thereof to a first immunoglobulin partner, so as to provide the altered immunoglobulin coding region and resulting expressed altered antibody with the antigenic specificity and neutralizing activity characteristic of the donor antibody. Donor antibodies suitable for use in this invention is a murine agonist monoclonal antibody designated as 15B8 and 13H10.

The term "acceptor antibody" refers to monoclonal or recombinant antibodies heterologous to the donor antibody, which contributes all, or a portion, of the nucleic acid sequences encoding its heavy and/or light chain framework regions and/or its heavy and/or light chain constant regions or V region subfamily consensus sequences to the first immunoglobulin partner. Preferably, a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs share or retain the same antigen binding specificity and/or agonist ability as the donor antibody from which they were derived, yet may exhibit increased affinity for the antigen. An exemplary process for obtaining analogs is affinity maturation by means of phage display technology as reviewed by Hoogenboom, *Trends in Biotechnology* 15, 62–70 (1997); Barbas et al., *Trends in Biotechnology* 14, 230–234 (1996); and Winter et al., *Ann. Rev. Immunol.* 12, 433–455 (1994) and described by Irving et al., *Immunotechnology* 2, 127–143 (1996).

By "sharing the antigen binding specificity or agonist ability" is meant, for example, that although mAb 15B8 or 13H10 may be characterized by a certain level of agonist activity, a CDR encoded by a nucleic acid sequence of 15B8 or 13H10 in an appropriate structural environment may have a lower or higher activity. It is expected that CDRs of 15B8 or 13H10 in such environments will nevertheless recognize the same epitope(s) as 15B8 or 13H10.

A "functional fragment" is a partial heavy or light chain variable sequence (e.g., minor deletions at the amino or carboxy terminus of the immunoglobulin variable region) which retains the same antigen binding specificity and/or agonist ability as the antibody from which the fragment was derived.

An "analog" is an amino acid sequence modified by at least one amino acid, wherein said modification can be chemical or a substitution or a rearrangement of a few amino acids (i.e., no more than 10) and corresponding nucleic acid sequences, which modification permits the amino acid sequence to retain the biological characteristics, e.g., antigen specificity and high affinity, of the unmodified sequence. Exemplary nucleic acid analogs include silent mutations which can be constructed, via substitutions, to create certain endonuclease restriction sites within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom or radioisotopes. Such effector agents may also be useful to increase the half-life of the altered antibodies, e.g., polyethylene glycol.

For use in constructing the antibodies, altered antibodies and fragments of this invention, a non-human species such as bovine, ovine, monkey, chicken, rodent (e.g., murine and rat) may be employed to generate a desirable immunoglobulin upon presentment with human Tie2 receptor or a peptide epitope therefrom. Conventional hybridoma techniques are employed to provide a hybridoma cell line secreting a non-human mAb to the Tie2 receptor. Such hybridomas are then screened for binding and agonist activity as described in the Examples section. Alternatively, fully human mAbs can be generated by techniques known to those skilled in the art and used in this invention.

Exemplary agonist mAbs of the present invention is mAb 15B8 and 13H10, murine antibodies which can be used for the development of a chimeric or humanized molecule. The 15B8 and 13H10 mAbs are characterized by agonist activity on human Tie2 receptor and subsequent activation of the receptor's signal transduction resulting in enhancement of angiogenesis. These mabs are produced by the hybridoma cell lines 15B8 and 13H10, respectively.

The present invention also includes the use of Fab fragments or F(ab')$_2$ fragments derived from mabs directed against Tie2 receptor as bivalent fragments. These fragments are useful as agents having agonist activity at the Tie2 receptor. A Fab fragment contains the entire light chain and amino terminal portion of the heavy chain. An F(ab')$_2$ fragment is the fragment formed by two Fab fragments bound by disulfide bonds. The mAbs 15B8 and 13H10 and other similar high affinity antibodies provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al., *Ann. Rev. Immunol.*, 12:433–455 (1994)) or via immunoglobulin chain shuffling (see, e.g., Marks et al., *Bio/Technology*, 10:779–783 (1992)), wherein the Fd or $v_H$ immunoglobulin from a selected antibody (e.g., 3G9) is allowed to associate with a repertoire of light chain immunoglobulins, $v_L$ (or $v_K$), to form novel Fabs. Conversely, the light chain immunoglobulin from a selected antibody may be allowed to associate with a repertoire of heavy chain immunoglobulins, $v_H$ (or Fd), to form novel Fabs. Tie2 receptor agonist Fabs can be obtained by allowing the Fd of mAb 15B8 or 13H10 to associate with a repertoire of light chain immunoglobulins. Hence, one is able to recover neutralizing Fabs with unique sequences (nucleotide and amino acid) from the chain shuffling technique.

The mAb 15B8 or 13H10 may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which facilitate insertion of mutagenized CDR and/or framework regions. These CDR-encoding regions can be used in the construction of the humanized antibodies of the invention.

The nucleic and amino acid sequences of the 15B8 heavy chain variable region is listed in SEQ ID NO: 1. The CDR amino acid sequences from this region are listed in SEQ ID Nos: 5, 6 and 7.

The nucleic and amino acid sequences of the 15B8 light chain variable region listed in SEQ ID NO: 3. The CDR amino acid sequences from this region are listed in SEQ ID Nos: 8, 9 and 10.

The nucleic and amino acid sequences of the 13H10 heavy chain variable region beginning at amino acid 7 is listed in SEQ ID NO: 11. The CDR amino acid sequences from this region are listed in SEQ ID Nos: 15, 16 and 17. The complete amino acid sequence of the 13H10 heavy chain variable region is listed in SEQ ID NO: 21.

The nucleic and amino acid sequences of the 13H10 light chain variable region listed in SEQ ID NO: 13. The CDR amino acid sequences from this region are listed in SEQ ID Nos: 18, 19 and 20.

Taking into account the degeneracy of the genetic code, various coding sequences may be constructed which encode the variable heavy and light chain amino acid sequences and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions to the DNA sequences. See, T. Maniatis et al., *Molecular Cloning: A Laboratory Manual*, Cold Spring Harbor Laboratory (1982), pp. 387–389. An example of one such stringent hybridization condition is hybridization at 4×SSC at 65° C., followed by a washing in 0.1×SSC at 65° C. for one hour. Alternatively, an exemplary stringent hybridization condition is 50% formamide, 4×SSC at 42° C. Preferably, these hybridizing DNA sequences are at least about 18 nucleotides in length, i.e., about the size of a CDR.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an Tie2 receptor antibody, preferably a high-affinity agonist antibody such as provided by the present invention, inserted into a first immunoglobulin partner such as a human framework or human immunoglobulin variable region.

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of the Tie2 receptor may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde and the like. Such techniques are known in the art and are described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified by techniques known to those skilled in the art to enhance expression.

A preferred altered antibody contains a variable heavy and/or light chain peptide or protein sequence having the antigen specificity of mAb 15B8 or 13H10, e.g., the $v_H$ and $V_L$ chains. Still another desirable altered antibody of this invention is characterized by the amino acid sequence containing at least one, and preferably all of the CDRs of the variable region of the heavy and/or light chains of the murine antibody molecule 15B8 or 13H10 with the remaining sequences being derived from a human source, or a functional fragment or analog thereof.

In a further embodiment, the altered antibody of the invention may have attached to it an additional agent. For example, recombinant DNA technology may be used to produce an altered antibody of the invention in which the Fc fragment or CH2 CH3 domain of a complete antibody molecule has been replaced by an enzyme or other detectable molecule (i.e., a polypeptide effector or reporter molecule) provided that the dimeric characteristic of the complete antibody molecule is retained.

The second immunoglobulin partner may also be operatively linked to a non-immunoglobulin peptide, protein or fragment thereof heterologous to the CDR-containing sequence having antigen specificity to the Tie2 receptor. The resulting protein may exhibit both antigen specificity and characteristics of the non-immunoglobulin upon expression. That fusion partner characteristic may be, e.g., a functional characteristic such as another binding or receptor domain or a therapeutic characteristic if the fusion partner is itself a therapeutic protein or additional antigenic characteristics.

Another desirable protein of this invention may comprise a complete antibody molecule, having full length heavy and light chains or any discrete fragment thereof, such as the Fab or F(ab')$_2$ fragments, a heavy chain dimer or any minimal recombinant fragments thereof such as an F$_v$ or a single-chain antibody (SCA) or any other molecule with the same specificity as the selected donor mAb, e.g., the 15B8 or 13H10 mAb. Such protein may be used in the form of an altered antibody or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin constant regions and variable framework regions from one source, e.g., the acceptor antibody, and one or more (preferably all) CDRs from the donor antibody, e.g., the 15B8 or 13H10 mAb. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the Tie2 receptor mAb (optionally modified as described) or one or more of the heavy or light chain CDRs. The engineered antibodies of the invention exhibit agonist activity.

Such engineered antibodies may include a humanized antibody containing the framework regions of a selected human immunoglobulin or subtype or a chimeric antibody containing the human heavy and light chain constant regions fused to the Tie2 receptor mAb functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the V region frameworks of the donor antibody or V region subfamily consensus sequences (on an amino acid basis) may be suitable to provide a heavy chain variable framework region for insertion of the donor CDRs. A suitable acceptor antibody capable of donating light chain variable framework regions may be selected in a similar manner. It should be noted that the acceptor antibody heavy and light chains are not required to originate from the same acceptor antibody.

Preferably, the heterologous framework and constant regions are selected from human immunoglobulin classes and isotypes, such as IgG (subtypes 1 through 4), IgM, IgA, and IgE. IgG1, k and IgG4, k are preferred. Particularly preferred is IgG4, k. Most particularly preferred is the IgG4 subtype variant containing the mutations S228P and L235E (PE mutation) in the heavy chain constant region which results in reduced effector function. This IgG4 subtype variant is known herein as IgG4PE. See U.S. Pat. Nos. 5, 624,821 and 5,648,260.

The acceptor antibody need not comprise only human immunoglobulin protein sequences. For instance, a gene may be constructed in which a DNA sequence encoding part of a human immunoglobulin chain is fused to a DNA sequence encoding a non-immunoglobulin amino acid sequence such as a polypeptide effector or reporter molecule.

A particularly preferred humanized antibody contains CDRs of 15B8 or 13H10 mAb inserted onto the framework regions of a selected human antibody sequence. For agonist humanized antibodies, one, two or preferably three CDRs from the 15B8 or 13H10 antibody heavy chain and/or light chain variable regions are inserted into the framework regions of the selected human antibody sequence, replacing the native CDRs of the human antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of ischemic diseases such as myocardial infarction or cerebral stroke or treatment of vascular insufficiency diseases, such as diabetes.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. These substitutions could be supplied by the donor antibody or consensus sequences from a particular subgroup.

In addition, the constant region may be altered to enhance or decrease selective properties of the molecules of this invention. For example, dimerization, binding to Fc receptors, or the ability to bind and activate complement (see, e.g., Angal et al., Mol. Immunol, 30, 105–108 (1993), Xu et al., J. Biol. Chem, 269, 3469–3474 (1994), Winter et al., EP 307434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant erythropoietic response in humans. Such antibodies are useful in the prevention of and for treatment of ischemic diseases such as myocardial infarction or cerebral stroke or treatment of vascular insufficiency diseases, such as diabetes.

Preferably, the variable light and/or heavy chain sequences and the CDRs of mAb 15B8 or 13H10 or other suitable donor mAbs and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody 15B8 or 13H10, is conventionally cloned and the DNA of its heavy and light chain variable regions obtained by techniques known to one of skill in the art, e.g., the techniques described in Sambrook et al., Molecular Cloning: A Laboratory Manual, 2nd edition, Cold Spring Harbor Laboratory (1989). The variable heavy and light regions containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin, are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody are identified using computerized databases, e.g., KABAT®, and a human antibody characterized by a homology to the V region frameworks of the donor antibody or V region subfamily consensus sequences (on an amino acid basis) to 15B8 or 13H10 is selected as the acceptor antibody. The sequences of synthetic heavy chain variable regions containing the CDR-encoding regions within the human antibody frameworks are designed with optional nucleotide replacements in the framework regions to incorporate restriction sites. This designed sequence is then synthesized using long synthetic oligomers. Alternatively, the designed sequence can be synthesized by overlapping oligonucleotides, amplified by polymerase chain reaction (PCR), and corrected for errors. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention may be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV or Rous Sarcoma virus promoter, and signal sequences, which can be derived from other known antibodies. Similarly, a second expression vector can be produced having a DNA sequence which encodes a complementary antibody light or heavy chain. Preferably, this second expression vector is identical to the first except with respect to the coding sequences and selectable markers, in order to ensure, as much as possible, that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by an appropriate assay such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the pUC series of cloning vectors, such as pUC19, which is commercially available from supply houses, such as Amersham or Pharmacia, may be used. Additionally, any vector which is capable of replicating readily, has an abundance of cloning sites and selectable genes (e.g., antibiotic resistance) and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV or Rous Sarcoma virus promoters) which direct the replication and expression of heterologous DNA sequences in selected host cells. These vectors contain the above-described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g., replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of E. coli are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3) and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., supra.

Bacterial cells may prove useful as host cells suitable for the expression of the recombinant Fabs of the present invention (see, e.g., Plückthun, A., *Immunol. Rev.*, 130, 151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of E. coli used for expression are well-known as host cells in the field of biotechnology. Various strains of B. subtilis, Streptomyces, other bacilli and the like may also be employed.

Where desired, strains of yeast cells known to those skilled in the art are also available as host cells, as well as insect cells, e.g. Drosophila and Lepidoptera, and viral expression systems. See, e.g. Miller et al., *Genetic Engineering*, 8, 277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently, surface plasmon resonance is employed to assess qualitative and quantitative binding of the engineered antibody to Tie2 receptor. Additionally, other in vitro assays such as the Matrigel vascularization model may also be used to determine agonist activity prior to subsequent human clinical studies performed to evaluate the persistence of the engineered antibody in the body despite the usual clearance mechanisms.

Following the procedures described for humanized antibodies prepared from 15B8 or 13H10, one of skill in the art may also construct humanized antibodies from other donor antibodies, variable region sequences and CDR peptides described herein. Engineered antibodies can be produced with variable region frameworks potentially recognized as "self" by recipients of the engineered antibody. Modifications to the variable region frameworks can be implemented to effect increases in antigen binding and agonist activity without appreciable increased immunogenicity for the recipient. Such engineered antibodies may effectively treat a human for ischemic diseases such as myocardial infarction or cerebral stroke or treatment of vascular insufficiency diseases, such as diabetes. Such antibodies may also be useful in the diagnosis of those conditions.

This invention also relates to a method for enhancing angiogenesis in an mammal, particularly a human, which comprises administering an effective dose of an Tie2 receptor monoclonal antibody having agonist activity. The mAb can include one or more of the engineered antibodies or altered antibodies described herein or fragments thereof.

The therapeutic response induced by the use of the molecules of this invention is produced by the binding to the Tie2 receptor and the subsequent agonist activity of the angiogenic process. Thus, the molecules of the present invention, when in preparations and formulations appropriate for therapeutic use, are highly desirable for persons susceptible to or experiencing ischemic diseases such as myocardial infarction or cerebral stroke or vascular insufficiency diseases, such as diabetes.

This invention also relates to a method for enhancing endothelial cell survival in a mammal comprising administering an effective dose of a Tie2 receptor agonist antibody.

This invention also relates to a method of enhancing hematopoietic or megakaryocytic cell proliferation in a mammal comprising administering and effective dose of a Tie2 receptor agonist antibody.

The mAb used in the methods of the invention can include one or more of the antibodies or altered antibodies described herein or fragments thereof. Preferably, the Tie2 receptor agonist antibody used in the methods of the invention has the identifying characteristics of mAb 15B8 or 13H10.

The altered antibodies, antibodies and fragments thereof of this invention may also be used in conjunction with other antibodies, particularly human mAbs reactive with other markers (epitopes) responsible for the condition against which the engineered antibody of the invention is directed.

Agonist antibodies to the Tie2 receptor would have the same therapeutic utility as the natural ligand, but would have the advantage of longer half-life and hence prolonged activity in vivo. These agonists can thus be employed to activate the biological cascade which results from receptor/ligand binding. The advantages of Tie2 receptor agonist antibodies include the ability to administer lower dosages of antibody than ligand, easier and less frequent administration of a pharmaceutic based on the agonist antibody, as well as easier purification.

The Tie2 receptor agonist antibodies of the invention can be formulated into pharmaceutical compositions and administered in the same manner as described for mature proteins. See, e.g., International Patent Application, Publication No. WO90/02762 (Mar. 22 1990). Generally, these compositions contain a therapeutically effective amount of an agonist antibody of this invention and an acceptable pharmaceutical carrier. Suitable carriers are well known to those of skill in the art and include, for example, saline. Alternatively, such compositions may include conventional delivery systems into which protein of the invention is incorporated. Optionally, these compositions may contain other active ingredients.

The therapeutic agents of this invention may be administered by any appropriate internal route, and may be repeated as needed, e.g., as frequently as one to three times daily for between 1 day to about three weeks to once per week or once biweekly. Preferably, the agonist antibody is administered less frequently than is the ligand, when it is used therapeutically. The dose and duration of treatment relates to the relative duration of the molecules of the present invention in the human circulation, and can be adjusted by one of skill in the art depending upon the condition being treated and the general health of the patient.

As used herein, the term "pharmaceutical" includes veterinary applications of the invention. The term "therapeutically effective amount" refers to that amount of a receptor agonist antibody, which is useful for alleviating a selected condition. These therapeutic compositions of the invention may be administered to mimic the effect of the normal receptor ligand.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously or intranasally.

Therapeutic agents of the invention may be prepared as pharmaceutical compositions containing an effective amount of the engineered (e.g., humanized) antibody of the invention as an active ingredient in a pharmaceutically acceptable carrier. In the compositions of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an engineered antibody of the invention. Actual methods for preparing parenterally administrable compositions are well known or will be apparent to those skilled in the art and are described in more detail in, for example, "Remington's Pharmaceutical Science", 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat anemia in a human or other animal, one dose of approximately 0.01 mg to approximately 20 mg per kg body weight of a protein or an antibody of this invention should be administered parenterally, preferably i.v. or i.m. Such dose may, if necessary, be repeated at appropriate time intervals selected as appropriate by a physician during the response period.

The present invention will now be described with reference to the following specific, non-limiting examples.

EXAMPLE 1

Preparation and Screening of Tie2 Agonist Monoclonal Antibodies

Mice (F1 hybrids of Balb/c and C57BL/6) were immunised subcutaneously with recombinant Tie2 extracellular domain-Fc fusion in RIBI adjuvant and boosted with the same. Alternatively, mice were immunized using Tie2 receptor-Fc fusion DNA and boosted with protein in RIBI adjuvant. A splenectomy was performed 3–4 days following the final immunization. Mouse spleen cells were used to prepare hybridomas by standard procedures, (Zola, H. Ed., Monoclonal Antibodies, CRC Press Inc. (1987)). Positive hybridomas were cloned by the limiting dilution method.

Immunoassay

To determine the specificity of the anti-Tie2 mAbs generated, 96-well plates were coated with Tie2-Fc and blocked. All the following incubations were performed in a shaker-incubator at RT. After washing the wells, Tie2-Fc or assay buffer and mAb/hybridoma supernatants were added in the presence of 20 ug/ml human IgG1 (to eliminate anti-Fc mAbs) and incubated for 60 min. After washing the wells, $Eu^{3+}$ labelled anti-mouse antibody in assay buffer was added for 60 min, the wells washed and then enhancer (Wallac) was added and incubated for 5 min at RT and the fluorescence measured. All positive hybridomas showed binding to Tie2.

Selection of Antibodies by BIAcore Binding Properties

BIAcore was used to select hybridomas and primary clones that bind to the external domain of the wild type Tie2 receptor. Antibodies were assessed for their ability to bind to Tie2-Fc by surface plasmon resonance using a BIAcore instrument. Rabbit anti-mouse IgG Fc specific antibody was immobilized on a sensor chip surface and mAb was injected, the refractive index units (RU; the RU are a direct measure of the amount of each protein which can bind) recorded, followed by injections of Tie2-Fc or IgG and record RU. The surface was regenerated with an injection of 15 ul 0.1M phosphoric acid. The above was repeated on a goat anti-human IgG Fc specific sensor chip surface, i.e. sequential addition of Tie2-Fc or IgG and monoclonal antibody. Two hybridoma supernatants showed the presence of high-affinity antibodies. The hybridoma cell lines and antibodies produced were designated 15B8 and 13H10.

Purification of Mabs

Monoclonal antibodies 15B8 and 13H10 were purified by protein-A chromatography per the manufacturer's instructions from the selected hybridoma supernatants. Mabs were >95% pure by SDS-PAGE.

Affinity Measurements of Monoclonal Antibody

The affinity of the purified mAbs was measured in the BIAcore. Using a flow rate of 10 ul/min, the mAb (diluted in HBS buffer) was injected over a rabbit anti-mouse IgG Fc surface, followed by buffer flow and the RU recorded. Tie2-Fc diluted in HBS buffer was then injected for 120s followed by buffer flow for 240s and regeneration of the sensor chip surface with an injection of 15 ul 0.1 M phosphoric acid. BIAcore software was used for association and dissociation-phase analysis. The murine monoclonal antibodies bound to soluble monomeric Tie2 receptor. The on-rates ($k_{ass}$) and off-rates ($k_{diss}$) were calculated. Together, these yield a calculated equilibrium constant ($K_D$) of 0.24 nM for mAb 15B8 and 3.1 nM for mAb 13H 10.

EXAMPLE 2

Functional Screening of Tie2 Agonist Monoclonal Antibodies

Whole-cell Activity Assay for the Tie2 Receptor

HEL cells (ATCC # TIB 180) are cultured at between 1 and $5\times10^5$ ml in RPMI-1640 medium supplemented with 2 mM glutamine and 10% FBS as a suspension culture. Sixteen to thirty-six hours prior to an experiment, the necessary number of cells are passaged into 0.5% FBS/RPMI medium. On the day of an experiment, cells are harvested and resuspended at a density of $0.5-1.0\times10^7$ cells ml in 0.5% FBS RPMI and seeded at 2–3 ml/well in six well plates.

Alternatively, Human Umbilical Vein Endothelial Cells (HUVECs) (Cell Systems—Kirkland, Wash.) may be used for the assay. HUVECs between passages 2 and 12, are plated at $2\times10^5$ and $1\times10^6$ cells per well in a six well plate in CS-C medium supplemented with 10% serum and endothelial cell growth factor (Cell Systems). After 24 hours the media is changed to CS-C medium supplemented only with 2% serum, and the cells are cultured overnight and used for assay the following day.

Cells are treated with ligand or antibody at appropriate concentrations for 10 minutes (exact time of exposure and concentration of ligand must be determined empirically for the experimental conditions). The contents of the wells are mixed briefly on a rocker (approx 30 seconds) and then incubated at 37° C. For each experiment there are appropriate controls run, such that there is at least one control for every gel (e.g. for a ten lane gel there will be up to eight experimental treatments, one control and one lane for markers) Appropriate controls depend on activities analyzed. For agonist effects, an untreated control is used for a base-line comparison. For antagonists or inhibitors of phosphorylation, a culture stimulated with an equivalent agonist (e.g. conditioned medium from cultured rheumatoid fibroblasts) alone, is used.

At the end of the 5–15 minute incubation period the plate is placed on ice. HEL cells are harvested by pipet. Media from HUVECs is removed, replaced with cold PBS, and the cells mechanically released from the plate surface with a policeman or cell scraper. The cells are spun down at 4° and the medium aspirated. The cell pellet is washed with cold PBS, centrifuged again, the PBS supernatant drawn off and the tubes/cell pellets submerged in a dry ice/ethanol bath. The cell pellet is removed to ice and allowed to thaw slightly. The pellet is resuspended in 500 μl of lysis buffer (RIPA lysis buffer: 50 mM Tris-HCl, pH 7.5, 150 mM NaCl, 1.0% NP-40, 0.5% deoxycholate, 0.1% SDS+ inhibitors: 1 mM Sodium Orthovanadate, 1 mM Sodium Fluoride, 1 mM EDTA,+protease inhibitors Sigma Mammalian cell protease inhibitor cocktail (#P8340) or a mix of PMSF, 1 mM aprotinin and Leupeptin—10 μg/ml). The suspension is sonicated for 5 pulses at a medium setting and returned to ice. The homogenate is centrifuged to remove un-lysed cells and the supernatants are transferred to microfuge tubes and kept on ice.

The phosphorylation state of the Tie2 receptor is determined by immunoprecipitation of the Tie2 receptor, isolation by electrophoresis and detection by anti-phosphotyrosine Ab, as detailed below (Harlow, E., and Lane, D. P., Antibodies—a Laboratory Manual, Cold Spring Harbor Laboratory Press: New York, 1988.). An alternative assay was done, using antibody against SH-PTP2 to precipitated Tie2 receptors. Approximately seven ug of Tie2 antibody (TIE2 polyclonal antibody, Santa Cruz, Biotechnology Cat.#sc-324) are added to each lysate and each sample is incubated for 1 hour while mixing at 4° C. Twenty ul of a protein A or proteinG agarose slurry is added and the samples incubated for an additional hour while mixing at 4° C. The agarose/antibody complexes are pelleted for 2' at 2000–5000 rpm and 4° C. in a microcentrifuge. The supernatant is carefully aspirated and the pellet is resuspended in 1 ml cold lysis buffer and again centrifuged. This wash step is repeated an additional two times. After the last aspiration, 40 ul 1×SDS-PAGE sample buffer (Laemli)+2.5% 2-mercaptoethanol is added. The sample is vortexed and boiled for 3 minutes. Thirty ul are run on a 7.5% SDS/polyacrylamide gel. The gel is then transferred to a nitrocellulose or PVDF membrane as per the manufacturer's instructions for Western blotting.

The blots are washed with PBS 0.05% tween-20 and then blocked with 5% Non-fat dry milk/PBS/tween for 1 hour at room temperature. The blots are then incubated with 1 ug/ml anti-phosphotyrosine antibody (e.g. Santa Cruz Biotech #SC508 or Upstate Biotech #05-321)-in PBS/0.05% tween for 1 hour. The blot is then washed 4 times with PBS/tween for 5 minutes each. The blot is incubated with an anti-mouse-HRP conjugate secondary antibody at the dilution recommended by the manufacturer, in PBS/tween for 1 hour. The blot is washed in PBS/tween, 4 times for 5 minutes each. After the last wash, the blot is developed by the ECL method (Amersham) or some equivalent.

After generating a satisfactory image, the blot is washed in 0.05% Tween 20-PBS.for 5 minutes, and then antibody is stripped using 100 mM 2-mercaptoethanol-2% SDS-62.5 mM Tris-HCL, pH6.8 for 30 minutes at 50° C. with occasional agitation. The blot is again washed in 0.05% Tween 20-PBS. In preparation for a second probing, the blots are blocked with 5% nonfat milk PBS/tween for 1 hour at room temperature, then incubated with 200 ng/ml anti-Tie2 antibody-3% nonfat milk PBS/tween for 1 hour. The blot is washed 4 times with PBS/tween for 5 minutes each, then incubated with an anti-rabbit-HRP antibody conjugate, diluted to the manufacturer's specifications in PBS/tween for 1 hour. After the blot is washed 4 times with PBS/tween for 5 minutes each, the image is developed by the ECL method.

Using a densitometer or graphics program (e.g. ImageQuant—Molecular Dynamics), each blot is scanned. The Tie-2 band is isolated and "boxed out" for each lane. The pixel volume or comparable measure for each sample is analyzed, for both Tie-2 staining and its corresponding phosphotyrosine staining. Also, an appropriate background region of the same dimensions is determined for each sample. After adjusting for background, phosphorylation is expressed as the ratio of phosphotyrosine staining, relative to the sample's corresponding Tie-2 staining.

The results indicated that mAb 1 B 8 consistently induced a maximum phosphorylation greater than two-fold over basal, at a concentration of 50 ug/ml. Discernible increases over the basal state are perceptible down to 1 ug/ml. Further, mAb 15B8 was able to stimulate association of the Tie-2 receptor with the signalling protein SH-PTP2 over a range of 1ug/mil to 50 ug/ml.

Measurement of Angiogenesis in vivo—Matrigel Vascularization Model

Angiogenesis is modeled in-vivo by placing an extracellular matrix gel, beneath the skin of a mouse for approximately one week, and then employing several measures to quantitate angiogenic invasion of the gel(Biancone, L, et al., J. Exp. Med. 186:147, 1997.). Briefly, reduced growth factor, endotoxin free Matrigel (Becton-Dickinson, Bedford, Mass.) is a gel at low temperatures. Antibodies or known angiogenic agents are mixed with the gel, such that they do not constitute more than 2% of the total volume. Eight week old or older, C57 female mice are administered 0.5 ml of the Matrigel by dorsal subcutaneous injection through chilled syringes. At physiological temperature, the liquid matrigel rapidly forms a solid and cohesive gel. After six days, the mice are sacrificed and the Matrigel plugs recovered. Angiogenesis is quantitated by analyzing the hemoglobin content of the gel by the method of Drabkin (Drabkin, D L and Austin, J H, J Biol Chem 112:51, 1935.)(Sigma, St. Louis, Mo.), or by staining and quantitating blood vessel with CD31 staining.

Normally, the matrigel remains mostly avascular. However, as shown in FIG. 1, mAb 15B8, at a concentration of 100 ug/ml, consistently stimulated an increase in vascular penetration between five and eight-fold, as measured by an increase in the gel's hemoglobin content. Neither a high affinity, but inactive mAb 11H10, nor the antagonist Mab, 12H8, at the same concentration stimulated angiogenesis significantly above control. Known positive controls such as Basic Fibroblast Growth Factor (bFGF) and Platelet Activating Factor (PAF), induce angiogenesis in these same experiments.

Endothelial Cell Survival

Human Umbilical Vein Endothelial Cells (HUVECs) (Cell Systems—Kirkland, Wash.), between passages 2 and 12, were plated at densities between $2 \times 10^5$ and $1 \times 10^6$ cells per well in a six well plate in CS-C medium (Cell Systems) supplemented with 10% fetal bovine serum (Hyclone) and endothelial cell growth factor (Sigma). After 24–48 hours the media was changed to CS-C medium supplemented only with 1–2% serum, and the cells were cultured overnight and used for assay the following day. For survival studies, they were treated with antibodies at indicated doses and cultured an additional period of time in serum free medium, then assessed for cell survival by visual inspection and trypan blue dye exclusion.

HUVEC cells are exquisitely sensitive to environmental conditions and require the addition of growth factors (e.g. aFGF) in culture medium in addition to fetal bovine serum. In the absence of such factors and serum the cells will not appreciably proliferate, and will rapidly undergo cell death. In our system, cells cultured overnight in minimal medium display significant morbidity, and are almost 100% non-viable within 24 hours.

The results indicated that mAb 15B8 promotes survival of endothelial cells. Addition of the antibody 15B8 at 50 ug/ml promoted enhanced survival over a 48-hour period. The cells remained adherent and maintained endothelial morphology.

Accordingly, Tie2 can play a key role in stabilizing the endothelium. Stimulation of Tie2 receptors in HUVECs grown in nutrient and growth factor-reduced medium by treatment with agonist mAb resulted in enhanced survival beyond similarly cultured control cells. Attachment to substrate and cellular morphology was also maintained. Stimulation of Tie2 receptors in a mammal would result in increased survival of existing vasculature, decreasing the effects of ischemic insults. Determination of the amount of antibody used to treat a mammal is within the purview of one ordinarily skilled in the art.

Growth of UT7 (GM-CSF) Cells

Megakaryocytes, their progenitors and megakaryblastic leukemia cells, such as UT7, express Tie2 receptors. A GM-CSF-dependent cell line, UT7(GM-CSF), was plated at $5 \times 10^4$ cells/ml in Iscove's Modified Dulbecco's Medium with 10% FCS. GM-CSF was used at either 10 ng/ml (optimal) or 5 ng/ml (sub-optimal) and Tie2 agonist mAb 15B8 at 1 ug/ml. At 24, 48 and 72 hours a sample of cells was removed from culture and counted.

The agonist mAb 15B8 alone did not have an effect on the growth of the cytokine-dependent hematopoietic cell line UT7 (GM-CSF). However, the 15B8 mAb synergized with suboptimal amounts of GM-CSF to increase UT7 (GM-CSF) cell number at 24 and 48 hrs of culture. Stimulation of Tie2 receptors in mammals would increase the proliferation of hematopoietic cells, including megakaryocyte progenitors in vivo, thereby increasing the number of blood cells and platelets produced. Determination of the amount of antibody used to treat a mammal is within the purview of one ordinarily skilled in the art.

EXAMPLE 3

Cloning and Sequencing of Anti-TIE2 Kinase Receptor Monoclonal Antibody Light and Heavy Chain cDNAs The amino acid sequences of the light- and heavy-chain N-termini were determined for the anti-TIE2 kinase receptor mAb 15B8 by means of protein microsequencing methodology. Pyroglutamic acid blocked N-termini were first deblocked enzymatically using pyroglutamate aminopeptidase.

Total 15B8 hybridoma RNA was purified, reverse transcribed and PCR amplified. For the heavy chain, the RNA/DNA hybrid was PCR amplified using a mouse IgG CH1-specific primer and a degenerate primer based on the N-terminal protein sequence. Similarly, for the light chain, the RNA/DNA hybrid was PCR amplified using a mouse C kappa primer and a degenerate primer based on the N-terminal protein sequence. PCR products of the appropriate size, i.e., ~350 were cloned into a plasmid vector, and sequenced by a modification of the Sanger method. In each case the sequence of VH and Vk clones were compared to generate a consensus 15B8 heavy chain variable region sequence (SEQ ID NOs: 1 and 2) and consensus 15B8 light chain variable region sequence (SEQ ID NOs: 3 and 4), respectively. The heavy chain CDR 1, 2 and 3 amino acid sequences are shown in SEQ ID NOs: 5, 6 and 7, respectively. The light chain CDR 1, 2 and 3 amino acid sequences are shown in SEQ ID NOs: 8, 9 and 10, respectively.

The amino acid sequence of the light-chain N-terminus was determined for the anti-TIE2 kinase receptor mAb 13H10 by means of protein microsequencing methodology. Pyroglutamic acid blocked N-termini were first deblocked enzymatically using pyroglutamate aminopeptidase.

Total 13H10 hybridoma RNA was purified, reverse transcribed and PCR amplified. For the heavy chain, the RNA/DNA hybrid was PCR amplified using a mouse IgG CH1-specific primer and a degenerate primer based on the N-terminal protein sequence. For the light chain, the RNA/DNA hybrid was PCR amplified using a mouse C kappa primer and a universal degenerate primer. PCR products of the appropriate size, i.e., ~350 were cloned into a plasmid vector, and sequenced by a modification of the Sanger method. The N-terminal amino acid sequence of the heavy chain was determined as described above and the VH clones were compared to generate a consensus 13H10 heavy chain variable region sequence. SEQ ID NOs: 11 and 12 list the 13H10 heavy chain variable region sequence beginning at amino acid 7. SEQ ID NO: 21 lists the complete amino acid sequence of the 13H10 heavy chain variable region. Comparison of Vk clones generated a consensus 13H10 light chain variable region sequence (SEQ ID NOs: 13 and 14), respectively. The heavy chain CDR 1, 2 and 3 amino acid sequences are shown in SEQ ID NOs: 15, 16 and 17, respectively. The light chain CDR 1, 2 and 3 amino acid sequences are shown in SEQ ID NOs: 18, 19 and 20, respectively.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An altered antibody comprising a heavy chain and a light chain, wherein the framework regions of said heavy and light chains are derived from at least one selected antibody and the amino acid sequences of the heavy chain complementarity determining regions (CDRs) are as set forth in SEQ ID NOs: 5, 6 and 7 and the amino acid sequences of the light chain CDRs are as set forth in SEQ ID NOs: 8, 9 and 10.

2. The altered antibody of claim 1 which is humanized.

3. The altered antibody of claim 1 which is human.

4. An antibody comprising a heavy chain variable region polypeptide as set forth in SEQ ID NO: 2 and a light chain variable region polypeptide as set forth in SEQ ID NO: 4.

5. An isolated polynucleotide encoding the polypeptide of SEQ ID NO: 2 or SEQ ID NO: 4.

6. A heavy chain CDR consisting essentially of an amino acid sequence as set forth in SEQ ID NO: 6 or 7.

7. An isolated polynucleotide encoding the CDR of claim 6.

8. A light chain CDR consisting essentially of an amino acid sequence as set forth in SEQ ID NO: 8, 9 or 10.

9. An isolated polynucleotide encoding the CDR of claim 8.

10. An antibody comprising a heavy chain variable region polypeptide as set forth in SEQ ID NO: 21 and a light chain variable region polypeptide as set forth in SEQ ID NO: 14.

11. An isolated polynucleotide encoding the polypeptide of SEQ ID NO: 21 or SEQ ID NO: 14.

12. A heavy chain CDR consisting essentially of an amino acid sequence as set forth in SEQ ID NO: 15, 16 or 17.

13. An isolated polynucleotide encoding the CDR of claim 12.

14. A light chain CDR consisting essentially of an amino acid sequence as set forth in SEQ ID NO: 18 or 20.

15. An isolated polynucleotide encoding the CDR of claim 14.

16. A pharmaceutical composition comprising the antibody of claims 4 or 10 and a pharmaceutically acceptable carrier.

17. An altered antibody comprising a heavy chain and a light chain, wherein the framework regions of said heavy and light chains are derived from at least one selected antibody and the amino acid sequences of the heavy chain CDRs are as set forth in SEQ ID NOs: 15, 16 and 17 and the amino acid sequences of the light chain CDRs are as set forth in SEQ ID NOs: 18, 19 and 20.

18. The altered antibody of claim 17 which is humanized.

19. The altered antibody of claim 17 which is human.

20. An antibody comprising a heavy chain and a light chain, wherein the amino acid sequences of the heavy chain CDRs are as set forth in SEQ ID NOs: 5, 6 and 7 and the amino acid sequences of the light chain CDRs are as set forth in SEQ ID NOs: 8, 9 and 10.

21. An antibody comprising a heavy chain and a light chain, wherein the amino acid sequences of the heavy chain CDRs are as set forth in SEQ ID NOs: 15, 16 and 17 and the amino acid sequences of the light chain CDRs are as set forth in SEQ ID NOs: 18, 19 and 20.

22. An isolated polynucleotide encoding the heavy chain of the altered antibody of claim 1.

23. An isolated polynucleotide encoding the light chain of the altered antibody of claim 1.

24. An isolated polynucleotide encoding the heavy chain of the altered antibody of claim 17.

25. An isolated polynucleotide encoding the light chain of the altered antibody of claim 17.

26. A cell line capable of secreting the antibody of claim 20.

27. A cell line capable of secreting the antibody of claim 21.

* * * * *